United States Patent
Polkinghorne et al.

(10) Patent No.: US 8,417,356 B2
(45) Date of Patent: *Apr. 9, 2013

(54) FIBROUS ELECTRODE MATERIAL

(75) Inventors: Jeannette C. Polkinghorne, Spring Lake Park, MN (US); Robert W. Warner, Woodbury, MN (US); James Q. Feng, Maple Grove, MN (US); James Lee Shippy, III, Wilmington, NC (US); Ljiljana Liliana Atanasoska, Edina, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 189 days.

This patent is subject to a terminal disclaimer.

(21) Appl. No.: 13/009,655

(22) Filed: Jan. 19, 2011

(65) Prior Publication Data

US 2011/0137389 A1 Jun. 9, 2011

Related U.S. Application Data

(63) Continuation of application No. 12/237,121, filed on Sep. 24, 2008, now Pat. No. 7,908, 016.

(60) Provisional application No. 60/981,221, filed on Oct. 19, 2007.

(51) Int. Cl.
*A61N 1/05* (2006.01)

(52) U.S. Cl. ...................................... 607/122

(58) Field of Classification Search ........... 607/115–122
See application file for complete search history.

(56) References Cited

U.S. PATENT DOCUMENTS

| | | | |
|---|---|---|---|
| 2,169,250 | A | 8/1939 | Izard |
| 4,043,331 | A | 8/1977 | Martin et al. |
| 5,187,032 | A | 2/1993 | Sasaki et al. |
| 5,522,879 | A | 6/1996 | Scopelianos |
| 5,529,579 | A | 6/1996 | Alt et al. |
| 5,554,176 | A | 9/1996 | Maddison et al. |
| 5,571,163 | A | 11/1996 | Helland |
| 5,951,597 | A | 9/1999 | Westlund et al. |
| 5,964,794 | A | 10/1999 | Bolz et al. |
| 6,295,474 | B1 | 9/2001 | Munshi |
| 6,718,628 | B2 | 4/2004 | Munshi |

(Continued)

FOREIGN PATENT DOCUMENTS

| | | |
|---|---|---|
| FR | 2696347 | 4/1994 |
| JP | 2142835 A | 5/1990 |

(Continued)

OTHER PUBLICATIONS

Aeos(R) ePTFE Expanded Polytetrafluoroethylene, Advanced Polymer Science for New Technologies, Zeus, 2 pages.

(Continued)

*Primary Examiner* — Brian T Gedeon
(74) *Attorney, Agent, or Firm* — Faegre Baker Daniels LLP

(57) ABSTRACT

A biomimetic electrode material including a fibrous matrix including a conductive polymer and an ion conducting polymeric material is described. The biomimetic electrode material may be used in a number of body-implantable applications including cardiac and neuro-stimulation applications. The biomimetic electrode material can be formed using electrospinning and other related processes. The biomimetic electrode may facilitate efficient charge transport from ionically conductive tissue to the electronically conductive electrode, and may induce surrounding tissue to attach or interface directly to the implanted device, increasing the biocompatibility of the device.

23 Claims, 5 Drawing Sheets

U.S. PATENT DOCUMENTS

| | | | |
|---|---|---|---|
| 6,743,273 | B2 | 6/2004 | Chung et al. |
| 6,790,528 | B2 | 9/2004 | Wendorff et al. |
| 6,856,840 | B2 | 2/2005 | Munshi |
| 6,999,821 | B2 | 2/2006 | Jenney et al. |
| 7,010,358 | B1 | 3/2006 | Kroll et al. |
| 7,689,291 | B2 | 3/2010 | Polkinghorne et al. |
| 7,908,016 | B2 | 3/2011 | Atanasoska et al. |
| 2002/0022826 | A1 | 2/2002 | Reynolds et al. |
| 2004/0013873 | A1 | 1/2004 | Wendorff et al. |
| 2004/0037813 | A1 | 2/2004 | Simpson et al. |
| 2004/0121528 | A1 | 6/2004 | Krulevitch et al. |
| 2004/0254513 | A1 | 12/2004 | Shang et al. |
| 2005/0107872 | A1 | 5/2005 | Mensah et al. |
| 2005/0131509 | A1 | 6/2005 | Atanassoska et al. |
| 2005/0175657 | A1 | 8/2005 | Hunter et al. |
| 2005/0192665 | A1 | 9/2005 | Spenser et al. |
| 2006/0035026 | A1 | 2/2006 | Atanasoska et al. |
| 2006/0165952 | A1 | 7/2006 | Dubrow |
| 2007/0048452 | A1 | 3/2007 | Feng et al. |
| 2007/0060815 | A1 | 3/2007 | Martin et al. |
| 2007/0067882 | A1 | 3/2007 | Atanasoska et al. |
| 2007/0239245 | A1 | 10/2007 | Borgaonkar et al. |
| 2008/0071338 | A1 | 3/2008 | Jiang et al. |
| 2008/0071349 | A1 | 3/2008 | Atanasoska et al. |
| 2009/0099634 | A1 | 4/2009 | Atanasoska et al. |
| 2011/0112617 | A1 | 5/2011 | Atanasoska et al. |

FOREIGN PATENT DOCUMENTS

| | | |
|---|---|---|
| JP | 7051391 A | 2/1995 |
| JP | 2005209458 A | 8/2005 |
| JP | 2005523116 A | 8/2005 |
| WO | WO 9716545 | 5/1997 |
| WO | WO 0123034 | 4/2001 |
| WO | WO 0141866 | 6/2001 |
| WO | WO 2004103470 | 12/2004 |
| WO | WO2006069322 A2 | 6/2006 |
| WO | WO2007028003 A2 | 3/2007 |
| WO | WO 2007130900 | 11/2007 |
| WO | WO 2008033546 | 3/2008 |
| WO | WO 2008036460 | 3/2008 |
| WO | WO 2009051945 | 4/2009 |

OTHER PUBLICATIONS

Berkland et al., Controlling surface nano-structure using flow-limited field-injection electrostatic spraying (FFESS) of poly (D,L-lactide-co-glycolide), Biomaterials 25: 5649-5658, 2004.

Boland, E. D., et al., "Electrospinning collagen and elastin: preliminary vascular tissue engineering", Front Biosci., 9, (May 1, 2004),1422-32.

Cogan, "Microelectrode coatings for neural stimulation and recording," Proceedings of the 25th Annual International Conference of the IEEE EMBS, Cancun, Mexico, Sep. 17-21, 2003, pp. 3798-3801.

Cuentas-Gallegos et al., "Physical and electrochemical characterization of nanostructured composites formed by Ti02 templates and PEDOT-PPS films," Electrochimica Acta 51: 3794-3801, 2006.

De Giglio, "Electropolymerization of pyrrole on titanium substrates for the future development of new biocompatible surfaces,"Biomiaterials 22: 2609-2616, 2001.

Dissertation by Salvatore Timpanaro, "Conductive Properties and Morphology of Conjugated Molecular Materials Studied by Local Probe Techniques," Universitat Potsdam, Oct. 2004, 96 pp.

Duan et al., "A study of intra-cochlear electrodes and tissue interface by electrochemical impedance methods in vivo," Biomaterials 25: 3813-3828, 2004.

Elizabeth et al., "Preparation and Characterization of PVC/PMMA Blend Polymer Electrolytes Complexed with LiN (C2F5S02)2,"Polimeros: Ciencia e Tecnologia 14(1): 1-7, 2004.

Geddes et al., "Criteria for the Selection of Materials for Implanted Electrodes," Annals of Biomedical Engineering 31:879-890, 2003.

Grafe, T. , et al., "Polymeric Nanofibers and Nanofiber Webs: A New Class of Nonwovens", INTC 2002: International Nonwovens Technical Conference (Joint INDA—TAPPI Conference), (Sep. 24-26, 2002.),1-13.

Hashmi et al., "Investigations on electrochemical supercapacitors using polypyrrole redox electrodes and PMMA based gel electrolytes," European Polymer Journal 41: 1373-1379, 2005.

Hashmi et al., "Polypyrrole and poly(3-methyl thiophene)-based solid state redox supercapacitors using ion conducting polymer electrolyte," Solid State Ionics 152-153: 883-889,2002.

Huang et al., "Electrochemical and spectroelectrochemical monitoring of supercapacitance and electrochromic properties of hydrous ruthenium oxide embedded poly(3,4-ethylenedioxythiophene )-poly(styrene sulfonic acid); composite," Electrochimica Acta 51: 3469-3476, 2006.

Huang et al., "Highly dispersed hydrous ruthenium oxide in poly (3,4-ethylenedioxythiophene)-poly(styrene sulfonic acid) for supercapacitor electrode," Electrochimica Acta 52: 1058-1063, 2006.

Huang et al., "Morphology and ionic conductivity of solid polymer electrolytes based on polyurethanes with various topological structures," Journal of Materials Science 39: 1221-1225, 2004.

Hwang et al., "Spectroscopic study on sputtered PEDOT-PSS: Role of surface PSS layer, "Organic Electronics 7:387-396,2006.

International Search Report and Written Opinion issued in PCT/US2008/077522, mailed Dec. 22, 2008, 8 pages.

International Search Report and Written Opinion issued in PCT/US2007/067757, mailed Oct. 26, 2007, 4 pgs.

International Search Report and Written Opinion issued in US/PCT/US2008/077527, mailed Jun. 15, 2010.

Invitation to Pay Additional Fees and, Where Applicable, Protest Fee with Partial International Search issued in US2008/077527, mailed Jul. 3, 2009,5 pages.

Inzel T et al., "Electron and proton conducting polymers: recent developments and prospects," Electrochimica Acta 45:2403-2421, 2000.

Kalluri, R. , "Basement membranes: structure, assembly and role in tumour angiogenesis", Nat Rev Cancer., 3(6), (Jun. 2003),422-33.

Lee et al., "Preparation and ionic conductivity of sulfonated-SEBS/Si02/plasticizer composite polymer electrolyte for polymer battery," Solid State Ionics 164: 65-72, 2003.

Lee, J. L., "Polymer Nanoengineering for Biomedical Applications", Annals of Biomedical Engineering,34(1), (2006), 75-88.

Liu et al., "Fundamental studies of novel inorganic-organic zwitterionic hybrids. 1. Preparation and characterizations of hybrid zwitterionic polymers," Journal of Non-Crystalline Solids 351: 3050-3059, 2005.

Liu, "Adsorption of bovine serum albumin and fibrinogen on hydrophilicity-controllable surfaces of polypyrrole doped with dodecyl benzene sulfonate-A combined piezoelectric quartz crystal impedance and electrochemical impedance study," Polymer 47: 3372-3381.

Louwet, "PEDOT/PSS: synthesis, characterization, properties and applications," Synthetic Metals 135-136: 115-117, 2003.

Mercier, I., et al., "Interactions of human skin fibroblasts with monomeric or fibrillar collagens induce different organization of the cytoskeleton", Exp Cell Res., 225(2), (Jun. 15, 1996), 245-56.

Mokrini et al., "Proton exchange membranes based on PVDF/SEBS blends,"Journal of Power Sources 154:51-58, 2006.

Murugan et al., "Enhancement of double-layer capacitance behavior and its electrical conductivity in layered poly (3,4-ethylenedioxy1hiophene)-based nanocomposites," Applied Physics Letters 87: 243511, 2005.

Oh et al., "New Interpenetrating Network-Type Siloxane Polymer Electrolyte," Electrochemical and Solid-State Letters 5(11): E59-E61, 2002.

Rajendran et al., "Characterization of plasticized PMMA-LiBF4 based solid polymer electrolytes," Bull. Mater. Sco.23(1): 27-29, Feb. 2000.

Rikukawa et al., "Proton-conducting polymer electrolyte membranes based on hydrocarbon polymers," Prog. Polym. Sci 25: 1463-1502, 2000.

Schindler, M., et al., "A synthetic nanofibrillar matrix promotes in vivo-like organization and morphogenesis for cells in culture", Biomaterials, 26(28), (Oct. 2005), 5624-5631.

Schmeichel, K. L., et al., "Modeling tissue-specific signaling and organ function in three dimensions", J Cell Sci., 116(Pt 12), (Jun. 15, 2003), 2377-88.

Shah, Parth N. et al., "Electrospinning of L-tyrosine polyurethanes for potential biomedical applications", Polymer 50 (2009) 2281-2289.

Shi, "A novel electrically conductive and biodegradable composite made of polypyrrole nanoparticles and polylactide", Biomaterials 25: 2477-2488, 2004.

Snaith et al., Morphological and electronic consequences of modifications to the polymer anode 'PEDOT:PSS,' Polymer 46: 2573-2578, 2005.

Snyder et al., "Polymer electrolytes and polyelectrolytes: Monte Carlo simulations of thermal effects on conduction," Solid State Ionics 147: 249-257, 2002.

Song, "Supercapacitive properties of polyaniline/Nafionihydrous Ru02 composite electrodes,"Journal of Power Sources 166: 297-301, 2007.

Sun et al., "Near-Field Electrospinning," NANO Letters 6(4): 839-842, 2006.

Vernitskaya, "Polypyrrole: a conducting polymer; its synthesis, properties and applications," Russian Chemical Reviews 66(5): 443-457, 1997.

Viswanathan et al., "Is Nafion® the only Choice?" Bulletin of the Catalysis Society of India 6: 50-66, 2007.

Yu et al., Production of Submicrometer Diameter Fibers by Two-Fluid Electrospinning, Advanced Materials 16(17):1562-1566, Sep. 2004.

Zong et al., "Electrospun fine-textured scaffolds for heart tissue constructs," Biomaterials 26: 5330-5338, 2005.

European Search Report issued in EP Application No. 11004980, completed Oct. 21, 2011.

Norliln, Anna, "Investigation of Electrochemical properties and performance of Stimulation/Sensing Electrodes for Pacemaker Applications" Doctoral Thesis, Royal Institute of Technology, Stockholm 2005.

Atanasoska, Lillian, "Choice of Electrode Coatings for Low Threshold Cardiac Pacing: In Vitro Efficiency Study", The Elctrochemical Society Meetings Abstracts, 2001-2, San Francisco, CA, Sep. 2-7, 2001.

Robblee, L.S. et al., "Activated IR: an electrode suitable for reversible change charge injection in saline solution", Journal of the electrochemical Society, 130(3), (1983), 731-733.

FIBROUS ELECTRODE MATERIAL

CROSS-REFERENCE TO RELATED APPLICATION

This application is a continuation of U.S. patent application Ser. No. 12/237,121, filed on Sep. 24, 2008, now published as Published Application No. 2009/0105796, entitled "Fibrous Electrode Material", which claims the benefit of Provisional Application Ser. No. 60/981,221, filed Oct. 19, 2007, entitled "Fibrous Electrode Material", which are both incorporated herein by reference in their entireties for all purposes.

TECHNICAL FIELD

This invention relates to body implantable medical devices, and more particularly, to implantable electrodes for sensing electrical impulses in body tissue or for delivering electrical stimulation pulses to an organ or a nerve.

BACKGROUND

Cardiac pacing leads are well known and widely employed for carrying pulse stimulation signals to the heart from a battery operated pacemaker or other pulse generating means, as well as for monitoring electrical activity of the heart from a location outside of the body. Electrical energy is applied to the heart via an electrode to return the heart to normal rhythm. Some factors that affect electrode performance include polarization at the electrode/tissue interface, electrode capacitance, sensing impedance, and voltage threshold. In all of these applications, it is highly desirable to optimize electrical performance characteristics at the electrode/tissue interface.

Surface and bulk materials currently used as electrodes for biomedical devices may result in inflammation in the vicinity of the implanted device and/or the formation of fibrous scar tissue. Such scar tissue may diminish signal transduction between the tissue and the device. One potential characteristic of inflammation and/or scar tissue is a deficiency of fluid at the electrode-tissue interface.

SUMMARY

According to one embodiment, the present invention is a medical electrical lead. The medical electrical lead includes a lead body having a conductor extending from a proximal end to a distal end. The proximal end of the lead body is adapted to be connected to a pulse generator. At least one electrode is operatively connected to the conductor. According to one embodiment of the present invention, the electrode includes a fibrous matrix including a conductive polymer and an ion conducting polymeric material. The electrode may also include a pseudo-capacitive material dispersed within the fibrous matrix.

According to another embodiment, the present invention is a method of forming an electrode. The method includes providing a collection substrate and a dispensing device. The dispensing device includes a first dispensing portion and a second dispensing portion. A first polymeric material is introduced into the first dispensing portion. A second polymeric material is introduced into the second dispensing portion. Next, an electrode needle is positioned into contact with the first polymeric material. An electrical potential difference is applied between the collection substrate and the electrode needle to cause localized charge injection into the first polymeric material. Optionally, an electrical potential difference may also be applied between the collection substrate and a second electrode needle (if used) to cause localized charge injection into the second polymeric material. The first and second polymeric materials are electro-statically discharged from the dispensing device toward the collection substrate.

According to yet another embodiment, the present invention is a method of forming an electrode material. According to this embodiment, the method includes electrospinning at least one polymeric material to form a plurality of fibers, collecting the electro-spun fibers on a collection substrate, and forming an electrode including a fibrous matrix from the electro-spun fibers.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
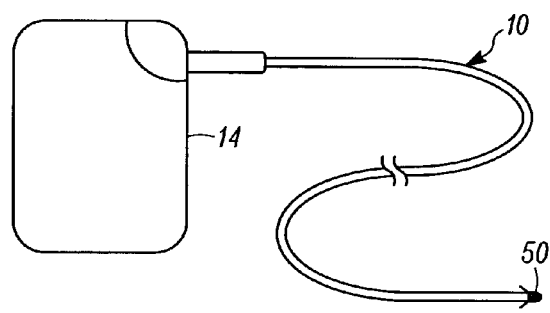
FIG. 1 is a schematic view of a lead and a pulse generator according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIG. 1 is a schematic view of a medical electrical lead 10 coupled to a pulse generator 14. The lead 10 includes one or more electrodes 50 to deliver pacing energy to a patient's heart and/or to sense and receive electrical signals from a patient's heart. Alternatively, the lead 10 could be utilized for neuro-stimulation or other body implantable applications.

The pulse generator 14, which can be implanted in a surgically-formed pocket in a patient's chest or other desired location, includes a power supply such as a battery, a capacitor, and electronic components to perform signal analysis, processing, and control. For example, the pulse generator 14 can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia.

Figure 2:
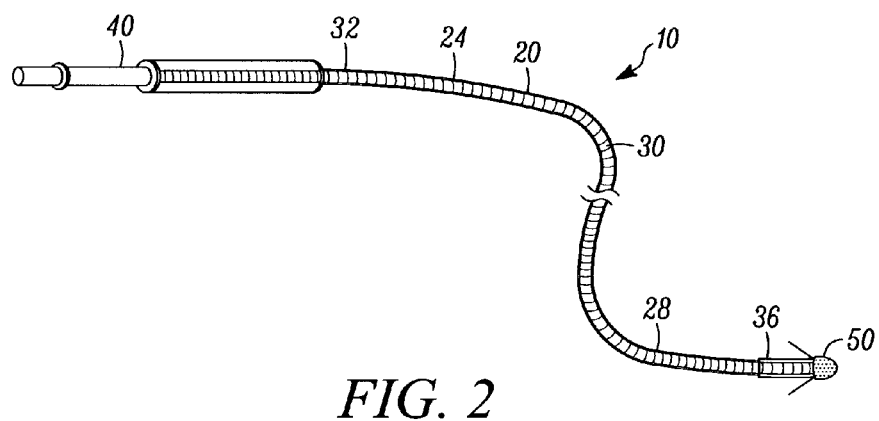
FIG. 2 is a partial cross-sectional view of the lead shown in FIG. 1 according to an embodiment of the present invention.

FIG. 2 is a partial, cross-sectional view of the lead 10 shown in FIG. 1. As shown in FIG. 2, the lead 10 includes an elongated, flexible lead body 20 having a proximal portion 24 and a distal portion 28. In one embodiment of the present invention, the lead body 20 includes a lumen for receiving a guiding element such as a guidewire or a stylet. The lead body 20 also includes one or more conductors 30 extending from a proximal end 32 to a distal end 36 of the lead body 20. The proximal end 32 is configured to be operatively connected to the pulse generator 14 via a connector 40.

The conductor 30 can include one or more conductive wires or fibers, which are operatively connected to one or more electrodes 50 located on the lead body 20. A plurality of discrete conductors may be utilized depending on the number of electrodes 50 employed.

Figure 3A:
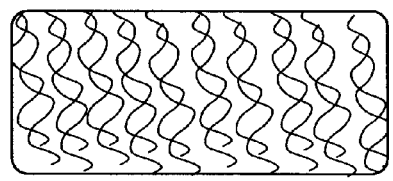
FIGS. 3A and 3B are cross-sectional, schematic views of an electrode according to various embodiments of the present invention.
Figure 3B:
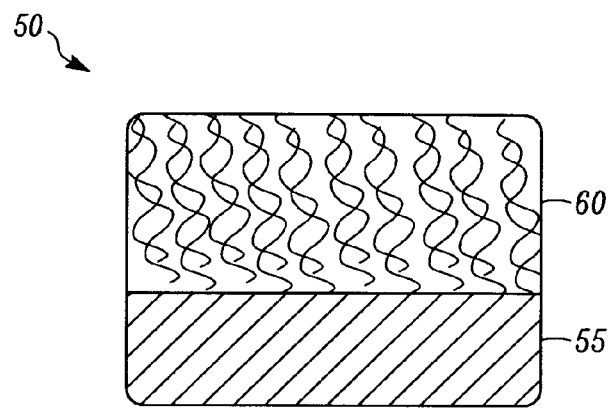

FIGS. 3A and 3B are cross-sectional, schematic views of the electrode 50 according to various embodiments of the present invention. According to one embodiment of the present invention, as shown in FIG. 3A, the electrode 50 includes a fibrous matrix of polymeric material including a conductive polymer and an ion conducting polymeric material. According to another embodiment of the present invention, as shown in FIG. 3B, the electrode 50 includes a conductive base 55 and a coating 60. The base 55 can be formed from platinum, stainless steel, MP35N, a platinum-iridium alloy or another similar conductive material. The coating 60, which is disposed on at least a portion of the conductive base 55, includes a fibrous matrix formed from a conductive polymer and an ion conducting polymeric material. According to one embodiment of the present invention, the coating is disposed over substantially all of the conductive base 55.

Conductive polymers, as used herein, include intrinsically conductive polymers and conductor-filled polymers. Examples of conductive filled polymers include polyurethanes, silicone elastomers, or other polymeric materials that are compounded with a conductive material such as carbon nanoparticles. Intrinsically conductive polymers are conductive without requiring a non-polymeric conductive filler or coating, such as a metallic compound or carbon. Intrinsically conductive polymers include alternating single and double bonds forming a conjugated backbone that displays electronic properties. Charge in intrinsically conductive polymers is transported along and between polymer molecules via charge carriers generated along the conjugated backbone.

Intrinsically conductive polymers may include dopants to enhance their conductivity. Dopants may also help to control the conductivity characteristics of the polymer. The conductivity of intrinsically conductive polymers can generally range from semi-conducting to super conducting, depending upon the doping levels. Some intrinsically conductive polymers may also exhibit a quasi-redox behavior that is highly reversible giving them pseudo-capacitive properties. Examples of intrinsically conductive polymers include, but are not limited to, the following: polypyrrole, polyacetylene, polythiophene, polyethylenedioxythiophene, poly (p-phenyl vinylene), polyaniline, polynapthalene, other suitable conductive polymers, and mixtures thereof.

According to one embodiment of the present invention, the conductive polymer is an intrinsically conductive polymer. According to another embodiment of the present invention, the conductive polymer is a conductive-filled polymer.

The inclusion of a conductive polymer into the fibrous matrix may increase its biocompatibility, reduce pacing thresholds, and improve sensing performance. Additionally, the inclusion of a conductive polymer may present an organic interface to biological tissue instead of a metallic interface (e.g. metallic electrode), which may facilitate a favorable biological response to the implant. The inflammatory and healing response of the tissue at the local site may be controlled and/or altered to reduce necrosis in the area next the to the lead and to reduce the thickness of any resultant fibrotic capsule.

As used herein, the term ion conducting polymeric material means any polymeric material capable of conducting ions and includes polymer electrolytes, polyelectrolytes, ionomers, and composites and combinations thereof.

In one embodiment, the ion conducting polymeric material is a polymer electrolyte. Polymer electrolytes can combine the desirable mechanical properties of polymers (e.g., ease of fabrication, low density, flexibility, etc.) with good conductivity. Polymer electrolytes are ionically conducting, solvent-free materials generally composed of alkali salts dissolved in a polymer matrix. According to one embodiment, a polymer electrolyte may include a lithium salt dissolved within a poly (ethylene oxide) (PEO) matrix. The ionic conductivity of the polymer electrolyte material is due to the mobility of cations and their counterions when subjected to an electric field within the polymer electrolyte material. According to other embodiments, useful polymer electrolytes can also include block co-polymers of polyethylene oxide with polyamide, polyimide, or polyurethane. Other examples include, but are not limited to, the following: polysiloxane, polymethyl methacrylate (PMMA), polyvinyl acetate (PVA), polyvinylpyrrolidone (PVP), and polylactic acid (PLA).

According to a further embodiment of the present invention, the polymer electrolyte is a hydrophilic polymer electrolyte. The presence of a hydrophilic polymer electrolyte within the fibrous matrix may correct any anomalous ion diffusion at the electrode/tissue interface resulting from a reduction of fluid as a consequence of inflammatory tissue responses at the local site, resulting in an increase in impedance and a distortion in the charge transfer characteristics.

According to another embodiment of the present invention, the ion conducting polymeric material is a polyelectrolyte. Polyelectrolytes, including ion exchange polymers, may be useful in forming the fibrous matrices according to the various embodiments of the present invention. Polyelectrolytes are polymers whose repeating units bear an electrolyte group. These groups will dissociate in aqueous solutions, making the polymers charged. Polyelectrolytes can be positively (cationic) or negatively (anionic) charged. Some polymer electrolytes include both cationic and anionic repeating groups. Exemplary polyelectrolytes include: polystyrene sulfonate (PSS), polyglutamic acid, Nafion®, and mixtures thereof.

The presence of an ion conducting polymeric material along with a conductive polymer within the fibrous matrix forms a matrix that is both a good ion and electron conductor. Additionally, the incorporation of an ion conducting polymeric material in the fibrous matrix may allow the fibrous matrix to be permeable to small molecules, resulting in an effective electrode surface area and the elimination of the abrupt electrode-tissue interface. The high electrode surface area combined with the elimination of the abrupt electrode-tissue interface may allow for a more efficient charge transfer process and may allow electric coupling to the surround neural or vascular tissue.

According to yet a further embodiment of the present invention, the fibrous matrix may include a plurality of conductive fibers doped with a hydrophilic polymer electrolyte.

According to another exemplary embodiment of the present invention, the fibrous matrix can also include a pseudo-capacitive material. A pseudo-capacitive material is a material that is capable of undergoing a reversible faradaic process, such as an oxidation/reduction (redox) reaction. Pseudo-capacitors are capable of storing large amounts of charge, and can serve as high or ultra-high capacitors. When the capacitance of a material is measured using cyclic voltammetry, capacitance is directly proportional to the measured current. Some conductive polymers such as polyaniline and polythiophenes can also behave as pseudo-capacitors. Exemplary pseudo-capacitive materials include, but are not limited to, transition metal oxides such as iridium oxide, ruthenium oxide, rhodium oxide, osmium oxide, titanium oxide, tantalum oxide, zirconium oxide, and combinations thereof. Other materials capable of enhancing the capacitive properties of the fibrous matrix include carbon, metal-carbon composites, nitrides, oxy-nitrides, or other materials with similar high capacitance characteristics. The incorporation of one or more of these materials into the fibrous matrix may further enhance the capacitance properties of the pseudo-capacitive materials.

The pseudo-capacitive material may be dispersed throughout the fibrous matrix in the form of microparticles or nanoparticles. In some embodiments, the dispersion of pseudo-capacitive particles can be a uniform dispersion of particles.

The amount of pseudo-capacitive material present in the fibrous matrix may be helpful for maintaining the electrode potential within a safe electrochemical window for pacing. The amount of pseudo-capacitive material present in the fibrous matrix should be sufficient to maintain the electrode potential within a safe electrochemical window for pacing. A safe electrochemical window for pacing can be defined as the potential range within which only reversible reactions occur. This can also be referred to as the charge injection limit. In general, the potential limits of the electrochemical window for pacing are the hydrolysis of water to oxygen and protons (anodic limit) and of hydrogen to hydroxide ions (cathodic limit) which is approximately 2V. Within this potential range a number of additional reactions may also occur.

| reduction | E°/volts |
|---|---|
| 1 $O_2 + 4H+ + 4e- \rightarrow 2H_2O$ | +1.229 |
| 2 $Ag+ + e- \rightarrow Ag$ | +0.7996 |
| 3 $Cu^{2+} + 2e- \rightarrow Cu$ | +0.3419 |
| 4 $Fe^{2+} + 2e- \rightarrow Fe$ | −0.447 |
| 5 $Zn^{2+} + 2e- \rightarrow Zn$ | −0.7628 |
| 6 $2H_2O + 2e- \rightarrow H_2 + 2OH-$ | −0.83 |

The voltage drop values at the electrode tissue interface remain within the cathodic and anodic potential limits of the hydrolysis of water resulting in a high capacitance of the electrode.

According to an embodiment of the present invention, the amount of pseudo-capacitive material present in the fibrous matrix should be sufficient to maintain the electrode potential within an electrochemical window of about 2 V. According to a further embodiment of the present invention, the fibrous matrix includes a pseudo-capacitive material present in an amount no greater than about 35 wt % of the total weight of the fibrous matrix.

Figure 4:
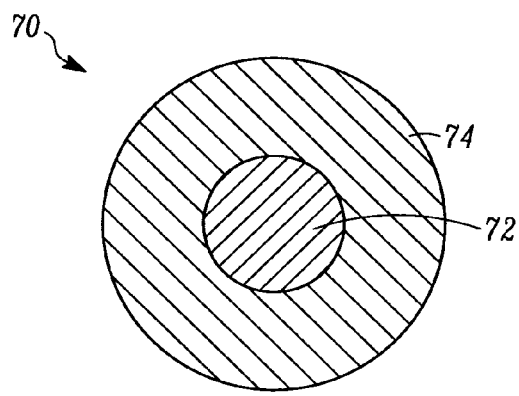
FIG. 4 is an end, cross-sectional view of a conductive fiber used to form an electrode according to an embodiment of the present invention.

According to an exemplary embodiment of the present invention, the fibrous matrix includes a plurality of fibers, each fiber including a core and a shell. FIG. 4 is a cross-sectional view of a fiber 70 including a core 72 and a shell 74. The core 72 includes a conductive polymer and the shell 74 includes a polymer electrolyte.

According to another embodiment of the present invention, the fibrous matrix can include a plurality of conductive polymer fibers inter-mixed with a plurality of polymer electrolyte fibers. According to yet another embodiment of the present invention, the fibrous matrix may include a core having a plurality of conductive polymer fibers surrounded by a shell including a plurality of polymer electrolyte fibers.

According to a further embodiment of the present invention, the pseudo-capacitive material can be dispersed within the conductive polymer fibers. According to yet another embodiment of the present invention, the pseudo-capacitive material may be dispersed within the ion conducting polymeric fibers.

Figure 5:
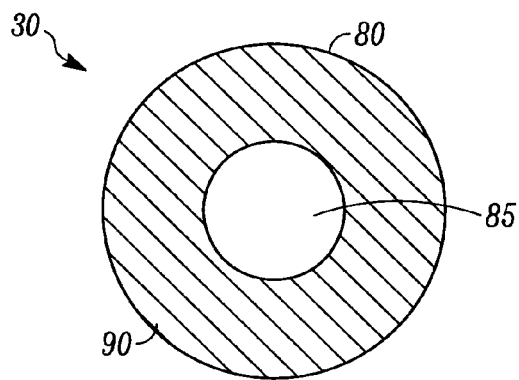
FIG. 5 is a cross-sectional view of a conductor including a conductive fiber.

According to other embodiments of the present invention, the conductor 30 extending from the proximal end 32 to the distal end 36 of the lead body 20 can also be formed from one or more conductive polymer fibers. FIG. 5 is a cross-sectional view of conductor 30 comprising a conductive fiber 80. According to one embodiment of the present invention, as shown in FIG. 5, the conductive fiber 80 includes a core 85 including a conductive polymer and a shell 90 including an insulative polymer. According to various exemplary embodiments, the conductive fiber 80 can include a single conductive fiber strand or a plurality of conductive fiber strands wound together to form a single conductive fiber.

A conductor 30 formed in this manner could extend from the proximal end 32 of the lead 10 to one or more electrodes 50. At each electrode 50, the conductive polymer fibers 80 could be combined with the polymer electrolyte fibers to form the fibrous matrix and the electrode site. In embodiments in which multiple electrodes 50 are used, multiple discrete conductors formed from the conductive polymer fibers could be utilized.

Figure 6:
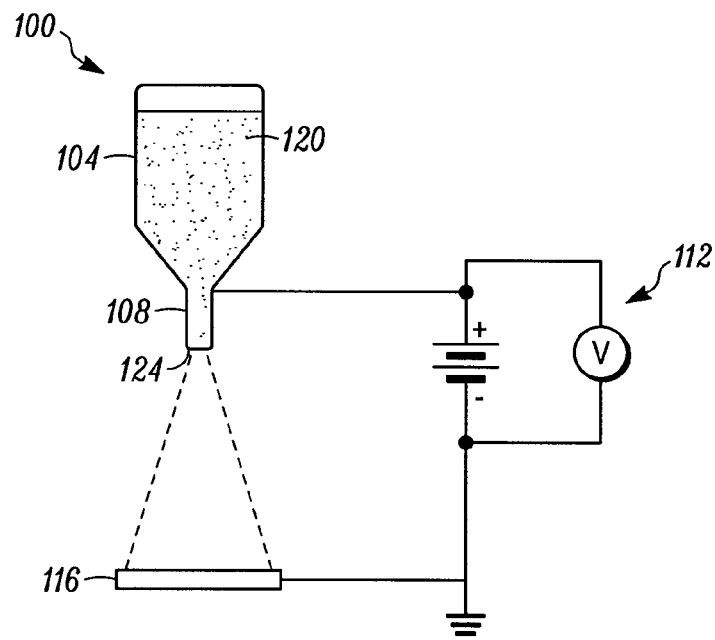
FIG. 6 is a schematic view of an apparatus used to form a fibrous matrix according to an embodiment of the present invention.

According to one embodiment of the present invention, an electrospinning technique may be used to form the fibrous matrix and/or conductor according to the various embodiments of the present invention as described above. Electrospinning of liquids and/or solutions capable of forming fibers, are shown and described, for example, in U.S. Pat. No. 4,043,331 which is incorporated herein by reference. FIG. 6 is a schematic view of a typical apparatus 100 used for electrospinning. The apparatus 100 includes a dispensing device 104, for example a syringe, having a metallic needle 108, a syringe pump (not shown), a high-voltage power supply 112, and a grounded collection substrate 116. A solution 120 containing one or more polymeric materials is loaded into the syringe and is then delivered to the needle tip 124 by the syringe pump, forming a suspended droplet at the needle tip 124.

At a characteristic voltage, the droplet forms a Taylor cone and a fine jet of polymeric material releases from the surface in response to the tensile forces generated by interaction of an applied electric field with the electrical charge carried by the jet. This jet can be directed to the grounded collector and collected as a continuous web of fibers.

Fibers ranging from about 50 nm to about 5 μm in diameter can be electrospun into a non-woven nanofiber mesh. Due to the small fiber diameters, electrospun fiber matrices inherently possess a very high surface area and a small pore size.

Electrospinning may also be used to produce fibers having a core-shell configuration, as described in Advanced Materials 2004, 16, No. 17, Sept 3, which is incorporated herein by reference in its entirety. To produce a fiber having a core-shell configuration, a spinneret that allows for the coaxial extrusion of two fluids is used. The spinneret includes concentric inner and outer tubes by which two fluids are introduced into the spinneret. The spinneret keeps the fluids separate as they are charged and emitted from the nozzle. At least one fluid, usually the fluid forming the shell, is an electrospinnable fluid.

According to another embodiment of the present invention, flow-limited, field-injection electrostatic spraying (FFESS) may be used to form the fibrous matrix. A FFESS apparatus and method is shown and described in US Published Application No. 2007/0048452, which is incorporated herein by reference in its entirety. FFESS allows electrically insulative materials, or materials having a low dielectric constant to be used to form fibrous materials because the localized field emission or field ionization can provide sufficient charge carries necessary for successful electrospinning. Additionally, FFESS may facilitate more precise deposition and controlled growth of polymeric nanofibers and other nanostructures. Pseudo-capacitive nanoparticles can be dispersed within the polymeric solution from which the fibers composing the fibrous matrix are formed. FFESS may also facilitate the fabrication of lead bodies having very small outer diameters.

Figure 7:
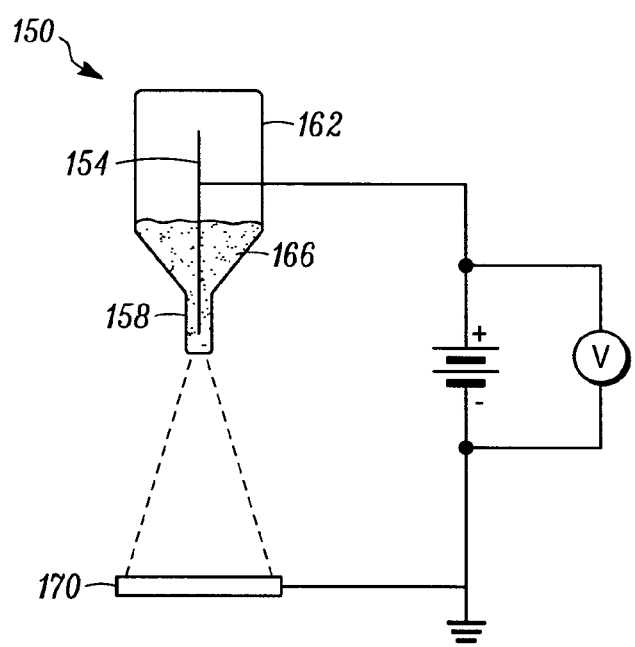
FIG. 7 a schematic view of an apparatus used to form a fibrous matrix according to another embodiment of the present invention.

FIG. 7 is a schematic view of an apparatus 150 that is suitable for use in FFESS processes. Unlike in conventional electrospinning techniques, a high-intensity electric field is applied at the tip of a needle 154 inserted within the tip 158 of the dispensing device 162 thus injecting charge into the surrounding solution 166. The resultant fibers are collected on a substrate 170 serving as a counter electrode.

Figure 8:
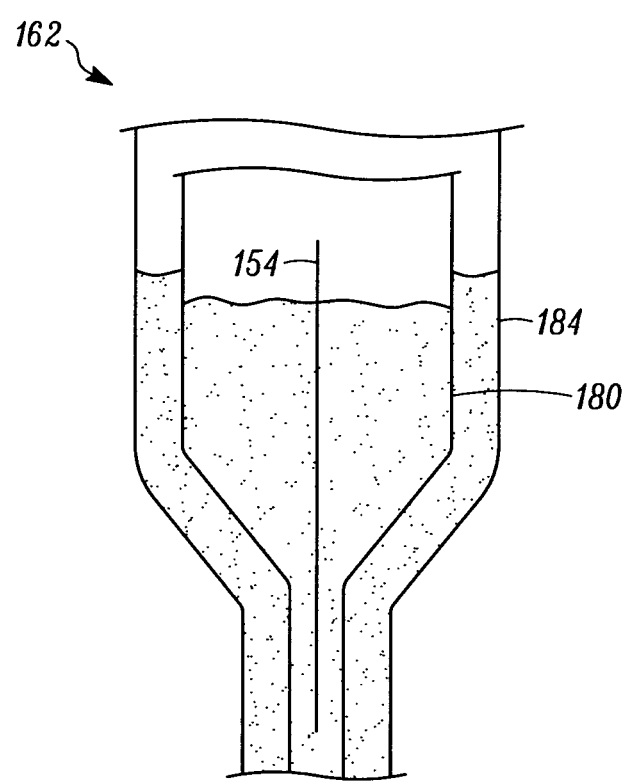
FIG. 8 is a close-up, schematic view of the dispensing device shown in FIG. 7 according to an embodiment of the present invention.

FFESS also may be used to produce fibers having a core-shell configuration. FIG. 8 is a close-up schematic view of the dispensing device 162 shown in FIG. 7 used to produce fibers having a core-shell configuration according to an embodiment of the present invention. As shown in FIG. 8, the dispensing device 162 can include a first dispensing portion 180 and a second dispensing portion 184. The first dispensing portion 180 may be positioned within the second dispensing portion 184. The needle 154 is inserted into the polymeric material requiring the charge injection. Two needles may be used if the polymeric materials in both the first and second dispensing portions 180, 184 require charge injection in order to form an electro-spun fiber. This configuration allows for fibers having a core including a first polymeric material surrounded by a second polymer material. For example, the dispensing device 162 as shown in FIG. 8 may be useful in forming a fiber or a fibrous matrix having a core including a conductive polymer and a shell including a polymer electrolyte or another ion conducting polymeric material, according to the various embodiments of the present invention, as described above.

Figure 9:
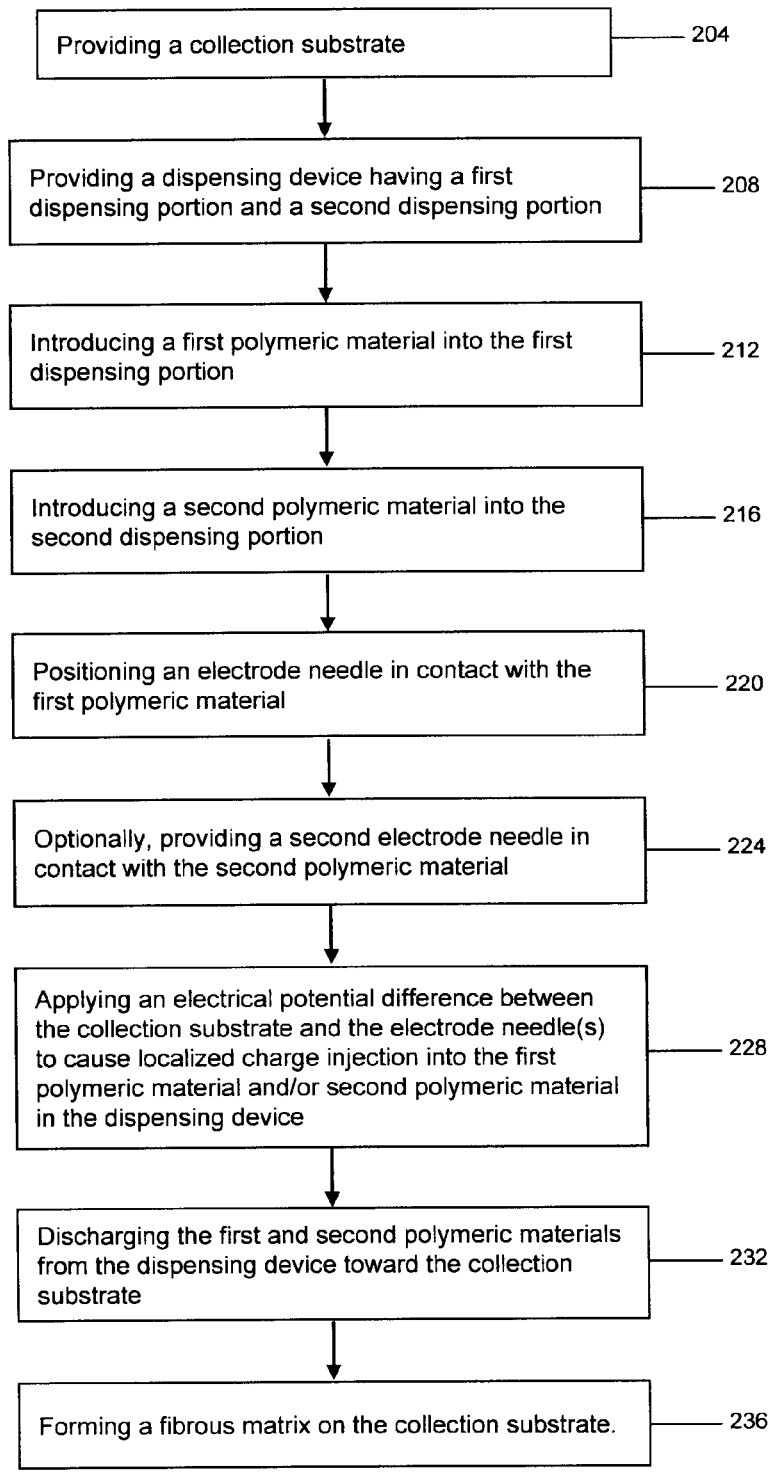
FIG. 9 is a flow chart of a method of making a fibrous matrix according an embodiment of the present invention.

FIG. 9 is a flow chart 200 of a method of forming a fibrous matrix using FFESS according to an embodiment of the present invention. First, a collection substrate is provided to collect the fibers formed during the electrospinning process (block 204). A dispensing device from which the polymeric solution is discharged is also provided (block 208). According to one embodiment of the present invention, the dispensing device includes a first dispensing portion and a second dispensing portion. A first polymeric material is introduced into the first dispensing portion of the dispensing device, typically via a pump or other suitable delivery device (block 212). Similarly, a second polymeric material is introduced into the second dispensing portion of the dispensing device (block 216). An electrode needle, such as a sharpened tungsten needle, is positioned within the first dispensing portion such that it is in contact within the first polymeric material (block 220). Depending on the physical properties of the second polymeric material, a second electrode needle may also be placed into contact with the second polymeric material (block 224). Finally, localized charge injection is induced into the first and/or second polymeric materials by applying an electrical potential difference between the collection substrate and the electrode needle(s) (block 228). The first and second polymeric materials are electro-statically discharged from the dispensing device and collected on the collection substrate in the form of fibers or a fibrous matrix (blocks 232 and 236). According to a further embodiment of the present invention, pseudo-capacitive particles may be dispersed in the first and/or second polymeric materials.

The electrode material, electrodes, and coatings contemplated by embodiments of the present invention include electrode materials, electrodes, and electrode coatings which have low biodegradability, low electrical impedance, long-term electrical stability under in vivo conditions, are mechanically soft (e.g. flexible), and are biomimetic. The large surface area can facilitate charge transfer between the electrode and target tissue. Additionally, the pliability and flexibility of the electrode and electrode coatings may facilitate decreased mechanical strain at the interface between the soft tissue and the hard device surface compared to a conventional electrode.

The electrode materials, electrodes, and electrode coatings of the present invention may provide electrodes and electrode coatings that are electrically stable over time following implantation in tissue. Additionally, the electrode materials, electrodes, and electrode coatings may be relatively non-biodegradable yet biocompatible, eliciting lower levels of immuno-reactivity than commonly used conductive substrate materials. According to various embodiments of the present invention, the electrodes or electrode coatings may be readily modified to contain a variety of bioactive agents. For example, proteins can be incorporated into the conducting polymer material via a variety of methods such as electro-chemical deposition, covalent linkage, and entrapment in the polymer matrix.

The electrode materials, electrodes, and electrode coatings may be used in a wide variety of applications including, but not limited to, the following: cardiac pacing and sensing, neuro-stimulation, cochlear stimulation, wound closure, pacing seeds, heart tissue constructs, and other applications in which improvement of the electrochemical interactions at the electrode-tissue interface may be desirable.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead comprising:
   an elongated lead body having a proximal end adapted to be coupled to a pulse generator and a distal end;
   at least one conductor extending within the lead body from the proximal end in a direction toward the distal end of the lead body; and
   at least one electrode located on the lead body operatively coupled to the at least one conductor, the electrode comprising a fibrous matrix including a plurality of fibers having a core comprising a first polymeric material surrounded by a shell comprising a second polymeric material.

2. The medical electrical lead according to claim 1, wherein the electrode further comprises a conductive base material and the fibrous matrix is disposed over and in contact with at least a portion of the conductive base material.

3. The medical electrical lead according to claim 1, wherein the first polymeric material comprises a conductive polymer.

4. The medical electrical lead according to claim 1, wherein the second polymeric material is an ion conducting polymeric material.

5. The medical electrical lead according to claim 1, wherein the first polymeric material comprises a conductive polymer selected from the group consisting of polypyrrole polyacetylene, polythiophene, polyethylenedioxythiophene, poly (p-phenyl vinylene), polyaniline, polynapthalene, and mixtures thereof.

6. The medical electrical lead according to claim 1, wherein the second polymeric material is selected from the group consisting of polystyrene sulfonate, polyglutamic acid, NAFION®, and mixtures thereof.

7. The medical electrical lead according to claim 1, wherein the electrode further comprises a pseudo-capacitive material dispersed within the fibrous matrix.

8. The medical electrical lead according to claim 1, wherein the fibrous matrix further includes a bioactive agent.

9. A body implantable device comprising:
   a conductor; and
   an electrode operatively coupled to the conductor, the electrode comprising a fibrous matrix including a plurality of fibers having a core comprising a first polymeric material surrounded by a shell comprising a second polymeric material.

10. The body implantable device according to claim 9, wherein the electrode further comprises a conductive base material and the fibrous matrix is disposed over and in contact with at least a portion of the conductive base material.

11. The body implantable device according to claim 9, wherein the first polymeric material comprises a conductive polymer.

12. The body implantable device according to claim 9, wherein the second polymeric material is an ion conducting polymeric material.

13. The body implantable device according to claim 9, wherein the first polymeric material comprises a conductive polymer selected from the group consisting of polypyrrole, polyacetylene, polythiophene, polyethylenedioxythiophene, poly (p-phenyl vinylene), polyaniline, polynapthalene, and mixtures thereof.

14. The body implantable device according to claim 9, wherein the second polymeric material is selected from the group consisting of polysiloxane, polymethyl methacrylate, polyvinyl acetate, polyvinylpyrrolidone, and polylactic acid.

15. The body implantable device according to claim 9, wherein the electrode further comprises a pseudo-capacitive material dispersed within the fibrous matrix.

16. The body implantable device according to claim 9, wherein the fibrous matrix further includes a bioactive agent.

17. A medical electrical lead comprising:
   a lead body having a proximal end adapted to be coupled to a pulse generator and a distal end; and
   a conductor extending from the proximal end in a direction toward the distal end of the lead body, the conductor comprising at least one fiber having a core comprising a first polymeric material surrounded by a shell comprising a second polymeric material.

18. The medical electrical lead according to claim 17, wherein the first polymeric material is a conductive polymer and the second polymeric material is an insulative polymer.

19. The medical electrical lead according to claim 17, wherein the conductor comprises a plurality of fibers, each fiber having a core comprising the first polymeric material surrounded by a shell comprising the second polymeric material.

20. The medical electrical lead according to claim 17, further comprising an electrode operatively coupled to the conductor, the electrode comprising a fibrous matrix including a conductive polymer.

21. A method of forming a fibrous electrode material comprising:
   electrospinning a first polymeric material and a second polymeric material to form a fibrous matrix comprising a plurality of electrospun fibers, each fiber having a core comprising the first polymeric material surrounded by a shell comprising the second polymeric material; and
   forming an electrode comprising the electrospun fibrous matrix.

22. The method according to claim 21, further comprising collecting the electrospun fibers on a surface of an electrode.

23. The method according to claim 21, further comprising coupling the electrode to a conductor.

* * * * *